United States Patent
Farzin-Nia et al.

(10) Patent No.: US 6,655,959 B2
(45) Date of Patent: Dec. 2, 2003

(54) ORTHODONTIC DEVICE FOR RETRACTION/EXTENSION OF TEETH

(75) Inventors: Farrokh Farzin-Nia, Inglewood, CA (US); Rohit Chaman Lal Sachdeva, Plano, TX (US)

(73) Assignee: Ormco Corporation, Orange, CA (US)

( * ) Notice: Subject to any disclaimer, the term of this patent is extended or adjusted under 35 U.S.C. 154(b) by 89 days.

(21) Appl. No.: 09/939,080

(22) Filed: Aug. 24, 2001

(65) Prior Publication Data

US 2003/0039939 A1 Feb. 27, 2003

(51) Int. Cl.[7] .................................................. A61C 7/00
(52) U.S. Cl. ........................................... 433/18; 433/21
(58) Field of Search ............................. 433/18, 20, 21, 433/7, 19

(56) References Cited

U.S. PATENT DOCUMENTS

| | | | |
|---|---|---|---|
| 3,618,214 A | 11/1971 | Armstrong | 433/19 |
| 3,798,773 A | 3/1974 | Northcutt | 32/14 |
| 3,936,938 A | 2/1976 | Northcutt | 32/14 A |
| 4,199,865 A | 4/1980 | Cain | 433/21 |
| 4,315,739 A | 2/1982 | Cain | 433/21 |
| 4,571,178 A | 2/1986 | Rosenberg | 433/18 |
| 5,040,975 A | 8/1991 | Etwein et al. | 433/3 |
| 5,074,784 A | 12/1991 | Sterrett et al. | 433/18 |
| 5,167,500 A | 12/1992 | Miura | 433/7 |
| 5,299,935 A | 4/1994 | Lokar | 433/18 |
| 5,312,247 A | 5/1994 | Sachdeva et al. | 433/7 |
| 5,505,616 A | 4/1996 | Harwell | 433/21 |
| 5,562,445 A | 10/1996 | DeVincenzo et al. | 433/19 |
| 5,620,320 A * | 4/1997 | Luse et al. | 433/5 |
| 5,645,422 A | 7/1997 | Williams | 433/7 |
| 5,711,667 A * | 1/1998 | Vogt | 433/19 |
| 5,738,514 A | 4/1998 | DeVincenzo et al. | 433/19 |
| 5,944,518 A * | 8/1999 | Sabbagh | 433/19 |
| 5,954,502 A | 9/1999 | Tuenge et al. | 433/16 |
| 6,402,510 B1 * | 6/2002 | Williams | 433/19 |

\* cited by examiner

*Primary Examiner*—Kevin Shaver
*Assistant Examiner*—Melba Bumgarner
(74) *Attorney, Agent, or Firm*—Wood, Herron & Evans, L.L.P.

(57) ABSTRACT

An orthodontic device for retraction or extension of teeth. The orthodontic device utilizes a spring and concentric sliding members to apply a biasing force to a patient's teeth in a manner that translates the teeth without rotation or tipping either tooth to which it is attached. A removable activation structure is adapted to hold the sliding members in a locked condition which maintains the device at a fixed length prior to fixation of the device to the teeth. When the activation structure is removed to provide a released condition, a corrective force is applied to the teeth for accomplishing an orthodontic treatment.

41 Claims, 4 Drawing Sheets

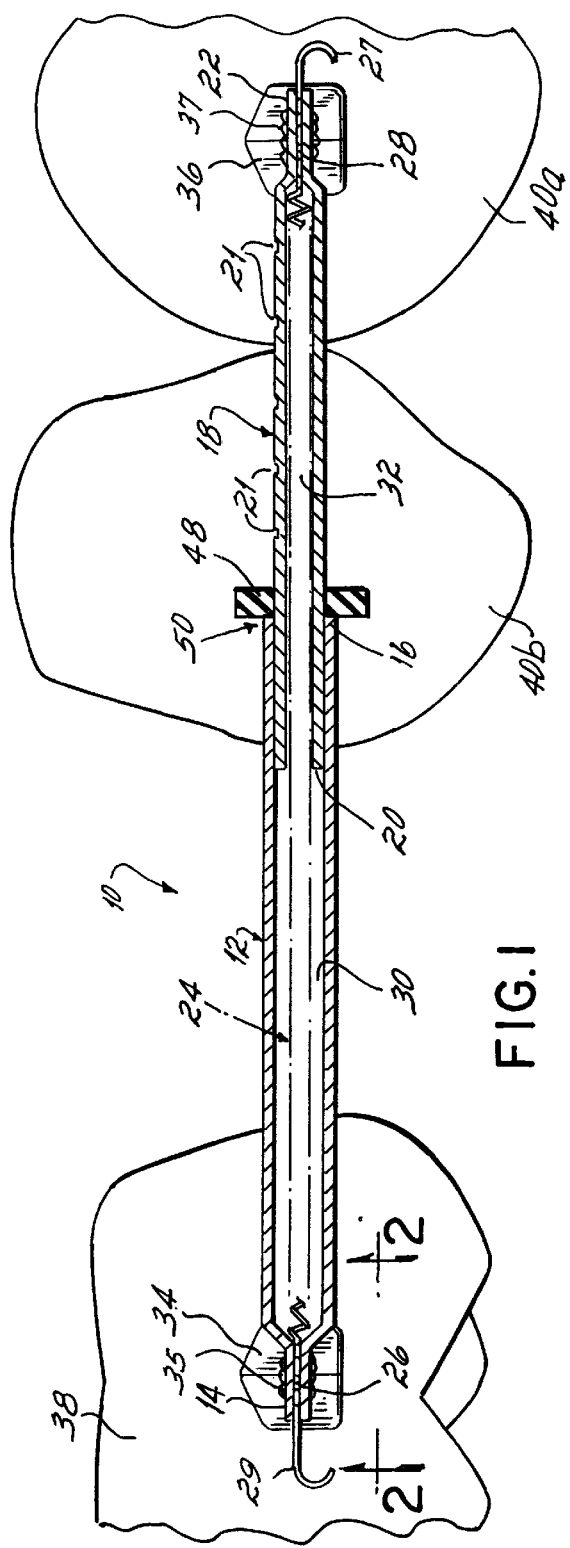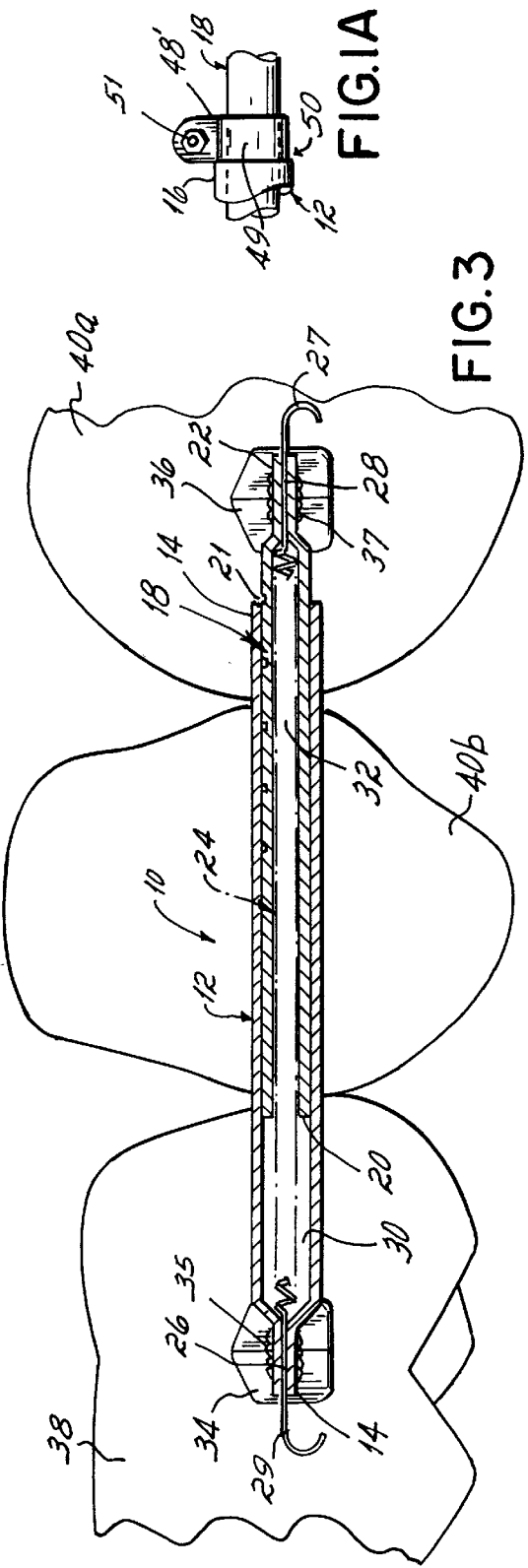

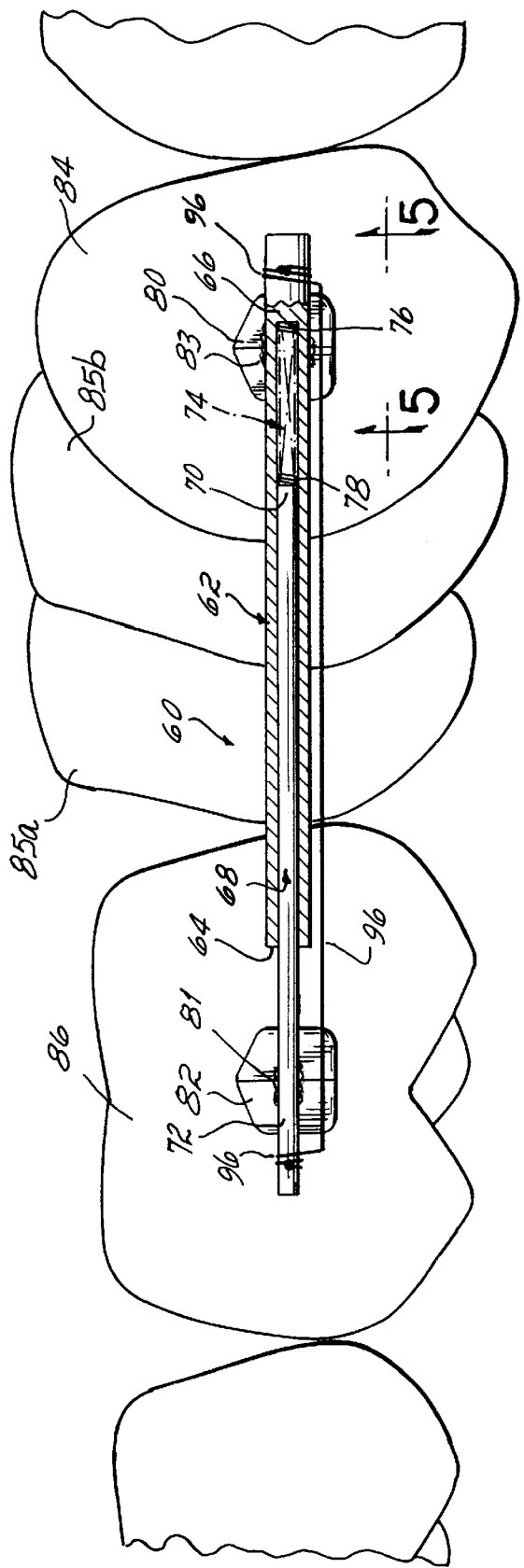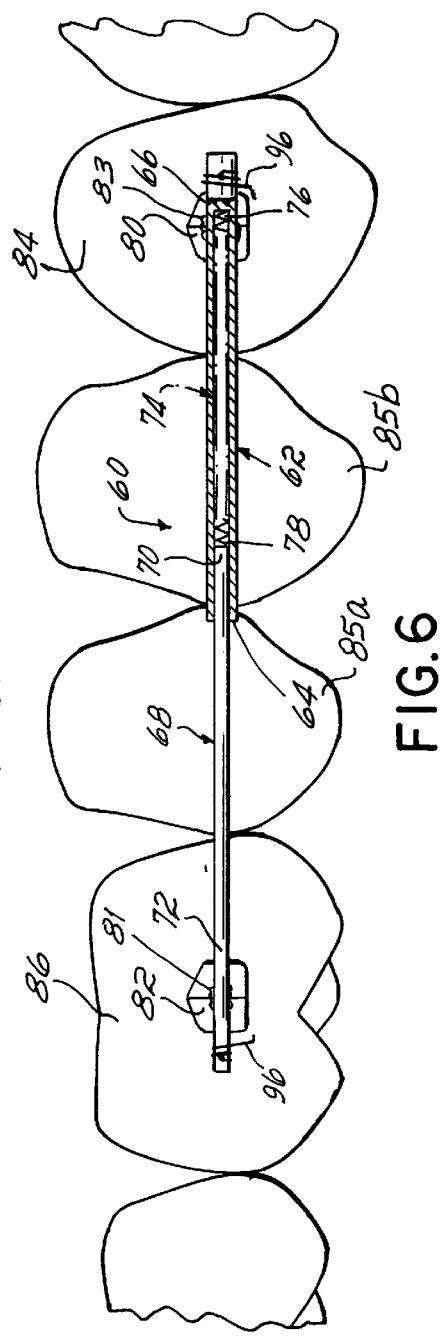

ORTHODONTIC DEVICE FOR RETRACTION/EXTENSION OF TEETH

FIELD OF THE INVENTION

The present invention generally relates to orthodontic devices and, more specifically, to intra-arch devices for treating malocclusions.

BACKGROUND OF THE INVENTION

Orthodontics is a branch of dentistry which deals with correcting irregularities in the arrangement of teeth, including the crowding of teeth and excessive spacings between nearby teeth. Orthodontic devices for treating such malocclusions are well known in the field of dentistry. Traditionally, orthodontic devices used for the movement of teeth to treat malocclusions includes a force-applying element that provides a continuous corrective force between one or more orthodontic pads, brackets or bands attached to a patient's teeth. The corrective force urges the teeth to move in a predetermined direction to correct the crowding or excess spacings. In some instances, orthodontic devices are used in intra-arch applications in which one or more teeth are moved relative to other teeth of the same jaw. In other instances, orthodontic devices are used in inter-arch applications in which one or more teeth or an entire dental arch is moved relative to the opposite dental arch.

The attachment of the orthodontic device usually involves the attachment of brackets to the teeth, either by adhesive bonding or the securing of bands around the circumference of various teeth. The brackets are usually each provided with a slot through which an arch wire is extended. Generally, one force-applying element is provided for the teeth of the upper jaw and one for the teeth of the lower jaw. The force-applying elements of conventional orthodontic devices are generally positioned on the labial side of a patient's teeth to avoid uncomfortable interference with the tongue. One type of force-applying element is an arch wire that is deformed and bent into a shape to attach to the brackets so as to supply the corrective force. Other force-applying elements include elastomeric bands, compression springs, and extension springs that are attached between adjacent brackets for the purpose of supplying the directional corrective force to move the teeth.

Arch wires have various shortcomings as force-applying elements. When the device is installed, the arch wire is shaped such that the arch wire applies an appropriate amount of corrective force in an suitable direction effective to move the teeth in the predetermined direction. During the course of a patient's treatment, the clinician periodically manually readjusts the device, usually by reshaping or bending the arch wires, to adjust the corrective force. Clinicians often have difficulties in creating these complex and precise bends in arch wires, which if not optimized, may compromise the quality of a patient's treatment and prolong the duration of that treatment.

Elastomeric bands have proven unsatisfactory as force-applying elements because the applied force degrades after only a few hours of exposure to the natural fluids inside a patient's mouth. Elastomeric bands also supply a displacement-dependent, non-constant force over a given range of motion as the teeth are moved into their new positions in the mouth. Another disadvantage is the patient can remove elastomeric bands so that the outcome of the orthodontic treatment is dependent upon patient cooperation. Elastomeric bands also fatigue such that the corrective force becomes too low to move the teeth efficiently or the bands may even break. As a result, the elastomeric bands must be frequently replaced or adjusted.

Traditional orthodontic devices which employ compression or extension springs also exhibit various deficiencies as force-applying elements. For example, the springs are exposed and the spring coils can pinch the tissue inside the patient's mouth as the spring expands and contracts. The pinching produces discomfort. In addition, food and other particles may be captured by the spring coils device and result in hygiene problems. Orthodontic devices utilizing steel springs have also tended to be rather complex, as typified by, for example, U.S. Pat. No. 5,299,935 to Lokar. Some prior art devices have utilized covers on the springs, such as U.S. Pat. No. 3,618,214 to Armstrong, but these devices have generally been designed for inter-arch use. Other devices, such as U.S. Pat. No. 5,562,445 to DeVincenzo et al., have utilized telescoping rods with the springs. These devices, however, have generally been designed to correct mandibular/maxillary detentions rather than merely repositioning teeth. Furthermore, these devices necessarily bridge more than one quadrant of a person's mouth.

Another significant problem with conventional orthodontic devices is that they generally do not apply a pure translational force to a tooth to which it is attached and, as a result, the tooth may rotate or tip as it translates to its new position. This problem arises because conventional orthodontic devices apply the corrective force at a tooth attachment point that does not necessarily coincide with the center of resistance of the tooth.

Accordingly, there is a need for a compact intra-oral orthodontic device, which is capable of translating a tooth without significant rotation and which is not susceptible to pinching the patient or allowing food or other particles to be trapped by the device.

SUMMARY OF THE INVENTION

The present invention provides an intra-arch orthodontic device for adjusting the distance between a first tooth and a second tooth located in a single quadrant of a mouth. The device includes a guide tube, an elongated member, and a spring positioned in an enclosed space provided by the engagement of the elongated member with the guide tube. The guide tube has a first end, an open second end, a hollow interior, and a first longitudinal axis extending along the hollow interior between the first end and the second end. The first end of the guide tube is adapted to be mounted to the first tooth. The elongated member has a third end, a fourth end, and a second longitudinal axis extending between the third end and the fourth end. The third end of the elongated member is slidably received within the second end of the guide tube to form the enclosed space. The fourth end of the elongated member is adapted to be mounted to the second tooth. The spring is positioned in the enclosed space and the spring biases the elongated member relative to the guide tube in a direction substantially parallel to the first and the second longitudinal axes. The magnitude of the biasing force applied by the spring is sufficient to adjust the distance between the first tooth and the second tooth when mounted thereto. The device can be configured to apply a biasing force that provides either a contraction or expansion of the spacing between adjacent teeth. A removable activation structure may be provided which is adapted to hold the elongated member and the guide tube in a locked condition until the activation structure is removed to provide a released condition in which the biasing force is applied.

The invention further contemplates a method for adjusting the spacing between at least the first and second teeth of a patient to a desired spacing using an orthodontic device as generally described above. The method comprises adjusting the distance between a first end and a second end to correspond to the spacing between the first tooth and the second tooth. The distance between the first end and the second end is locked by placing the activation structure in a locked condition. The first end and the second end are affixed to the first tooth and second tooth, respectively. The activation structure is placed in a released condition to apply a biasing force between the first tooth and the second tooth.

One advantage of the present invention is that by bonding directly to the teeth, the device does not require the use of an arch wire. Therefore, the device may be installed on either the labial or the lingual side of the teeth. Another advantage of the present invention is that the flexible connection between the mounting pads and the tube or pin arrangement allows the device to accommodate the natural arch of a patient's teeth. Another advantage of the present invention is that it permits pure translation of a tooth desired to be moved without the undesirable rotation of the tooth that is typical of existing orthodontic devices. The device of the present invention may be attached at or near the center of resistance of the tooth so that rotation is avoided as the teeth move under the influence of the applied corrective force.

These and various other objectives, advantages and features will become more readily apparent to those of ordinary skill in the art, upon review of the following detailed description of the preferred embodiments taken in conjunction with the accompanying drawings.

BRIEF DESCRIPTION OF THE DRAWINGS

FIG. 1 is a cross-sectional view of an orthodontic device of the present invention.

FIG. 1A is a view of a portion of FIG. 1 illustrating an alternative embodiment of an activation structure for use with the present invention.

FIG. 3 is a cross-sectional view of the orthodontic device of FIG. 1 in which the device is in a contracted position.

FIG. 4 is a cross-sectional view of an orthodontic device of the present invention.

FIG. 6 is a cross-sectional view of the orthodontic device of FIG. 4 in which the device is in an expanded position.

DETAILED DESCRIPTION

Figure 2:
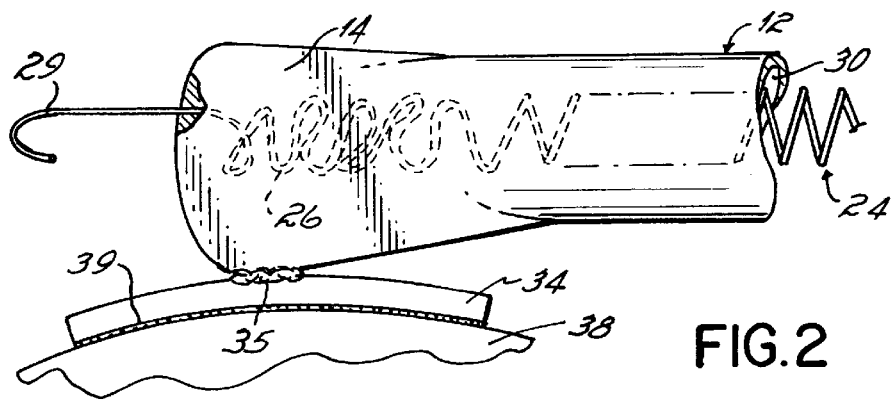
FIG. 2 is a view taken along line 2—2 of FIG. 1.

With reference to FIGS. 1 and 2, an intra-arch orthodontic device 10 of the present invention for contracting the space between adjacent teeth in one quadrant of a person's mouth includes a guide tube or first tube 12 having a first end 14, which may be substantially closed, and a second end 16, which is open. A second tube 18 has a first end 20, which is open, and a second end 22, which may be substantially closed. The second tube 18 is in a sliding contact with the first tube 12 in that the first end 20 of the second tube 18 is inserted into the first end 14 of the first tube 12. The outer diameter of the second tube 18 is slightly smaller than the inner diameter of the first tube 12 so as to permit a sliding, telescoping fit therebetween. Second tube 18 has a series of spaced-apart positioning marks 21 on an outer surface of the plate which guide the clinician in monitoring the telescoping movement of the tubes 12, 18 as the corrective force moves the teeth to which device 10 is attached. For example, tube 18 may be provided with a series of positioning marks 21 having a uniform spacing of about 0.5 mm. The positioning marks 21 may comprise any marking structure, such as indentations or indelible surface markings, that does not interfere with the telescoping movement of tube 18 relative to tube 12.

With continued reference to FIGS. 1 and 2, the second end 16 of the first tube 12 is adhesively bonded with a quantity 35 of a dental adhesive to a mounting pad 34 and the second end 22 of the second tube 18 is adhesively bonded with a quantity 37 of the dental adhesive to a mounting pad 36. Suitable dental adhesives include an ultraviolet-curable dental adhesives. The mounting pads 34, 36 are mounted to spaced-apart teeth 38, 40a, respectively, using a quantity 39 (FIG. 2) of the dental adhesive. The mounting pads 34, 36 have a mesh and foil construction typical of the type used in orthodontic procedures and may be fabricated from an AISI 316 stainless steel. However, various attachment structures are contemplated by the present invention for securing the tubes 12, 18 to teeth 38, 40a, respectively.

In one embodiment of the present invention, the second end 16 of the first tube 12 and the second end 22 of the second tube 18 may be attached to the respective one of the mounting pads 34, 36 via a flexible connection 41 (FIGS. 2A and 2B), as will be described below. In another embodiment, a side wall portion of the second end 16 of tube 12 and a side wall portion of the second end 22 of tube 18 are bonded with an adhesive, such as an ultraviolet-curable dental adhesive, directly to the enamel of the respective one of teeth 38, 40a and without the intervening pads 34, 36. In yet another embodiment, a side wall portion of the second end 16 of tube 12 and a side wall portion of the second end 22 of tube 18 are attached to the pads 34, 36 by conventional methods, such as adhesive bonding, welding, brazing, soldering and the like, before adhesively bonding pads 34, 36 to teeth 38, 40a, respectively, with a dental adhesive. In yet another embodiment, conventional brackets (not shown) may be welded to pads 34, 36 and second ends 16, 22 attached to the brackets by welding, brazing, soldering, adhesive bonding, and the like before pads 34, 36 are adhesively bonded to teeth 38a, 40, respectively. In yet another embodiment, conventional orthodontic bands (not shown but similar to band 55 shown in FIG. 7) may be positioned on the teeth 38, 40a and the second ends 16, 22 of each of tubes 12, 18 attached to a respective bracket on each band by adhesive bonding, brazing, welding, soldering or the like before mounting the bands to teeth 38, 40a. Such orthodontic bands and brackets are commercially available from, for example, Ormco Corporation (Orange, Calif.).

Figure 7:
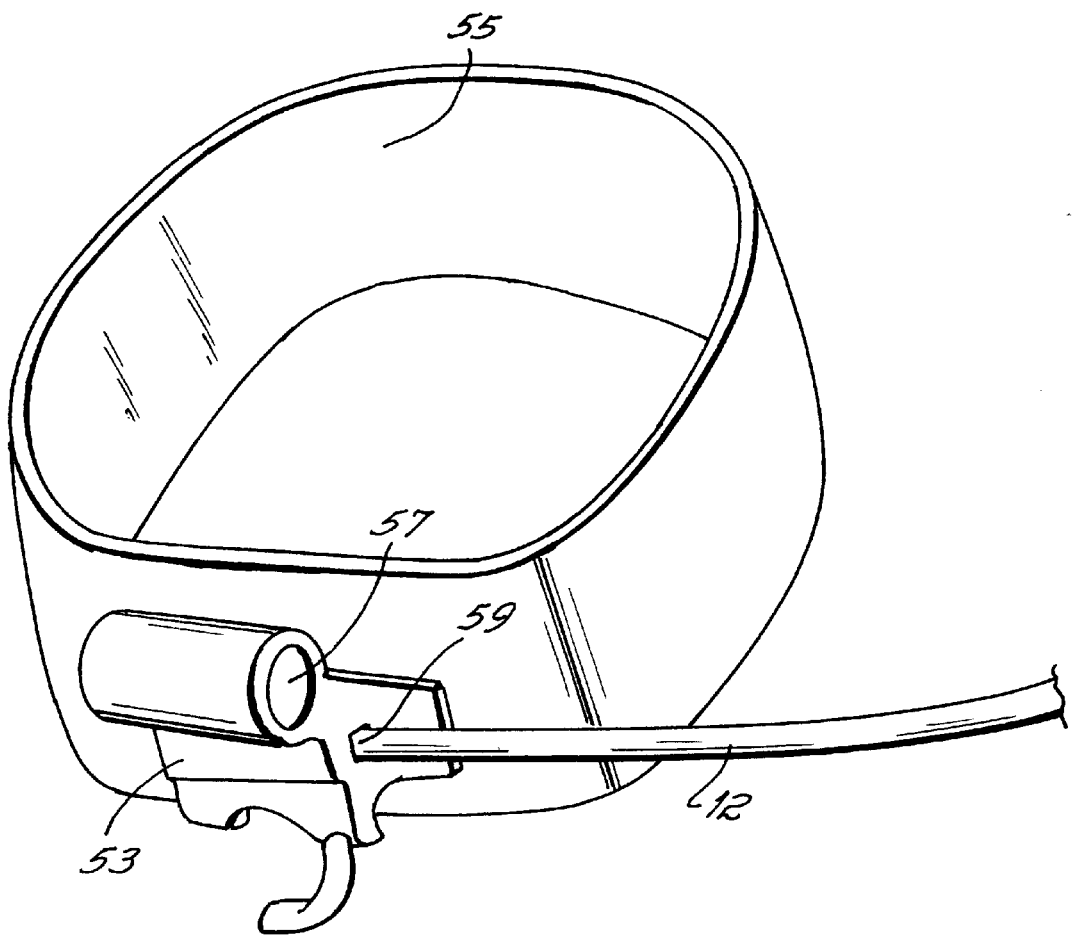
FIG. 7 is a perspective view of an alternative embodiment of an attachment structure for attaching the orthodontic device to a tooth, in which the tooth is not shown.

In yet another embodiment and with reference to FIG. 7, a buccal tube 53 may be attached to a convention band 55 for mounting the second ends 16, 22 of tubes 12, 18 to the teeth 38, 40a, respectively. In this embodiment, each of the second ends 16, 22 may be secured within one of the channels or bores 57, 59 which are commonly found in conventional buccal tubes, using a conventional fastening technique including, but not limited to, adhesive bonding, brazing, soldering and welding. Buccal tubes suitable for use as buccal tube 53 are commercially available from, for example, Ormco Corporation (Orange, Calif.). The bores 57, 59 permit permit additional orthodontic devices, such as arch wires and facesbows, to be attached to the band 55. In other embodiments, the buccal tube 53 may be attached to a pad, similar to pads 34, 36, or a bracket. It is understood that combinations of these various attachment structures are contemplated by the present invention, such as, for example, brazing second end 16 of device 10 to a buccal tube 53 carried by a side wall of a band 55 prior to attaching the band 55 to tooth 38 and adhesively bonding the second end 22 to pad 36, which is itself adhesively bonded to tooth 40a.

Figure 5:
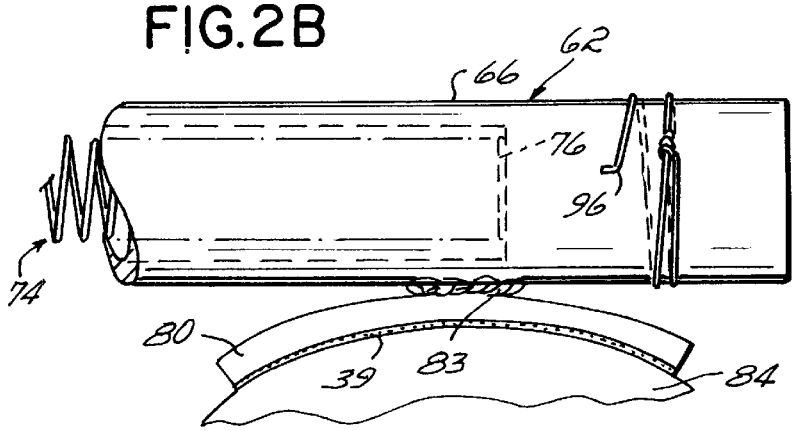
FIG. 5 is a view taken along line 5—5 of FIG. 4.

With continued reference to FIGS. 1 and 2, an extension spring 24 having a first end 26 and a second end 28 is disposed within the enclosed space defined by the hollow interiors of the first and second tubes 30, 32. The ends 26, 28 of spring 24 are secured to the second ends 16, 22 of tubes 12, 18 respectively. Preferably, the first end 26 of the spring 24 is secured to the first tube 12 by a crimping the second end 16 of the tube 12 to capture a portion of the spring 24. The second end 28 of the spring 24 is likewise secured by crimping the second end 22 of the second tube 18 to capture a portion on the spring 24. The first and second ends 26, 28 of spring 24 may also be attached to tubes 12 and 18, respectively, by conventional fastening methods such as welding, brazing, soldering, adhesive bonding, and the like. Although tubes 12, 18 are illustrated in FIG. 1 as having a linear construction, the present invention is not so limited. For example, tubes 12, 18 may provided with a curvature as shown, for example, for tube 12 in FIG. 7. The curvature in tubes 12, 18 permits device 10 to accommodate a non-linear telescoping movement as the teeth to which device 10 is attached move in a curved path in response to the corrective force applied by spring 24. This is particularly useful for situations in which exceptionally crowded teeth are being expanded by an expansion orthodontic device, to be described below with regard to intra-arch orthodontic device 60 (FIGS. 4–6).

Tubes 12 and 14 are fabricated from a metal or metal alloy, such as a stainless steel, a titanium alloy, a brass, or the like. In one specific embodiment, tubes 12, 14 are made from an AISI 304 stainless steel. Spring 24 may be constructed or fabricated from any metal or metal alloy suitable for constructing a compression spring, including stainless spring steel alloys, titanium alloys, and any metal alloy exhibiting pseudoelastic properties. Exemplary pseudoelastic metal alloys include, but are not limited to, nickel-titanium alloys. In one embodiment, spring 24 is constructed so that it is not permanently deformed or set after being expanded more than about 100 percent of its free length. In another embodiment, spring 24 is constructed to provide about 1500 grams, or less, of spring force to a patient's teeth when installed.

In one embodiment, the end 26 of the spring 24 may project a short distance beyond the opening in the second end 16 of the tube 12 and the opposite end 28 of the spring 24 may project a short distance beyond the opening in the second end 22 of the tube 18. The projection distances should be limited such that any tissue impingement with ends 26, 28 is prohibited or limited. The ends 26, 28 may each optionally be deformed to form loops or hooks 27, 29, as illustrated in FIG. 1. Alternatively, the present invention contemplates that individual lengths of a wire (not shown) may be affixed to each of the first and second ends 16, 22 and the protruding end of each wire bent to provide the hooks 27, 29, respectively. A linking structure (not shown), such as an elastomeric band or a chain, may be attached between hooks 27, 29 to supply a supplemental biasing force so as to increase the magnitude of the corrective force applied between teeth 38, 40a. In addition, a linking structure shown may be likewise attached between, for example, hook 27 and a similar hook on another device (not shown but which may be similar to device 10) located in another portion of the patient's mouth, such as located in the same quadrant of the opposite jaw to which device 10 is attached.

With continued reference to FIG. 1, an activation structure 48 is removably attached to the device 10 at an interface 50 between the tubes 12, 18 and is adapted to hold the second tube 18 substantially stationary relative to first tube 12 and in a locked condition so as to prevent relative sliding, telescoping movement therebetween. Specifically, the compressive engagement between activation structure 48 and tube 18 is sufficient to prevent second tube 18 from telescopically sliding into the first tube 12 under the biasing force applied by the spring 24 at least until the mounting pads 34, 36 have been bonded securely to the teeth 38, 40a. When the activation structure 48 is removed, the first tube 12 assumes a released condition relative to the second tube 18 for sliding relative movement and a corrective force is applied between teeth 38, 40a. In one embodiment, the activation structure 48 comprises one or more elastomeric annular rings, as shown in FIG. 1, which are configured and sized to compressively engage an outer diameter of second tube 18, which are removed by cutting. In another embodiment, the activation structure 48 may comprise an elastomeric sleeve or tube which compressively fits about an outer circumference of second tube 18. In yet another embodiment, the activation structure 48 may comprise a ring fabricated from a metal or a metal alloy that can be crimped with a conventional crimper, such as pliers, to compressively engage the exterior of second tube 18 and that is removed by cutting with a conventional cutting tool.

With reference to FIG. 1A, another embodiment of an activation structure 48' is a releasable clamp consisting of a flexible band 49 fabricated from a resilient material, such as a thin sheet of a metal or a metal alloy, and wrapped about the second tube 18 near the interface 50. Opposite ends of the flexible band 49 are joined in a conventional manner by a conventional fastener 51. Tightening the fastener 51 causes the band 49 to apply a compressive force to the exterior of tube 18. Loosening the fastener 51 releases the band 49 for sliding movement along the length of tube 18. Removing the fastener 51 permits removal of the metal band from tube 18. This embodiment of the activation structure 48' may be used as a stop for the telescoping movement of the tubes 12, 18 after the orthodontic device 10 has been deployed in a patient's mouth. Orthodontic treatments are generally accomplished in several stages, each of which may require a spring 24 of differing characteristics, such as spring stiffness, so as to vary the corrective force applied between teeth 38, 40a. To facilitate various stages of the orthodontic treatment, the activation structure 48 may be loosened to deploy device 10 and then repositioned along the length the second tube 18. As the spacing between teeth 38 and 40a decreases under the influence of the corrective force, the device 10 will eventually be disabled when an end surface of first tube 12 abuts against the motion-limiting stop provided by the structure 48, which removes the corrective force acting between teeth 38 and 40a. Device 10 can then be detached from teeth 38, 40a and the spring 24 exchanged for a different spring 24 having different characteristics. The device 10 can then be reattached to teeth 38, 40a and deployed to initiate a subsequent stage of the orthodontic treatment. This embodiment of the activation device 48' may be particularly useful in combination with the positioning marks 21 in providing for well-defined, prospective stop positions during the orthodontic treatment.

With reference to FIGS. 1 and 3, the operation of intra-arch orthodontic device 10 will be described. Device 10 is designed to be deployed in a single quadrant of a person's mouth to correct malocclusions of the type where it is desired to move teeth to close a space between adjacent ones of the teeth. The initial separation between mounting pads 34, 36 is determined, for example, by using a model of the patient's teeth or other suitable method, such as with reference to an x-ray image of the patient's teeth. Force is applied to device 10 to position the mounting pads 34, 36 at the desired separation and the activation structure 48 is positioned on second tube 18 at the interface 50 between the first and second tubes 12, 18. The presence of the activation structure 48 prevents the second tube 18 from sliding into the first tube 12 under the biasing action of the spring 24.

Mounting pads 34 and 36 are fixed to the teeth 38, 40a of the patient by bonding the pads 34, 36 to the teeth 38, 40a with respective quantities 39 of the dental adhesive. Mounting pad 34 is generally fixed to a molar tooth 38 to serve as an anchor, and mounting pad 36 is generally fixed to the tooth 40a, which is desired to move in response to the corrective force applied by spring 24. With the relative separation between mounting pads 34, 36 thus established, device 10 is installed in the patient's mouth using respective quantities 35, 37 of dental adhesive to bond mounting pads 34, 36 to teeth 38, 40a. Once the dental adhesive has cured, activation structure 48 is removed, for example by severing with a cutting implement, so that device 10 is no longer constrained in the locked condition and will assume the activated or released condition. In this manner, spring 24 applies a corrective force to the patient's teeth 38, 40b so as to cause the teeth to move together and close any spaces between the teeth 38, 40a, 40b, as depicted in FIG. 3. Because the corrective force is constrained by the telescoping, sliding relative movement between tubes 12 and 18 to be substantially linear, the movement of tooth 38 relative to tooth 40a is substantially translational, without rotating or tipping either of teeth 38, 40a. Because an arch wire is not required for applying the corrective force, device 10 may be installed on either the labial or lingual side of teeth 38, 40a. As described above, the activation device 48 may be utilized to provide a stop for the movement that is useful in defining stages of a particular orthodontic treatment.

Figure 2A:
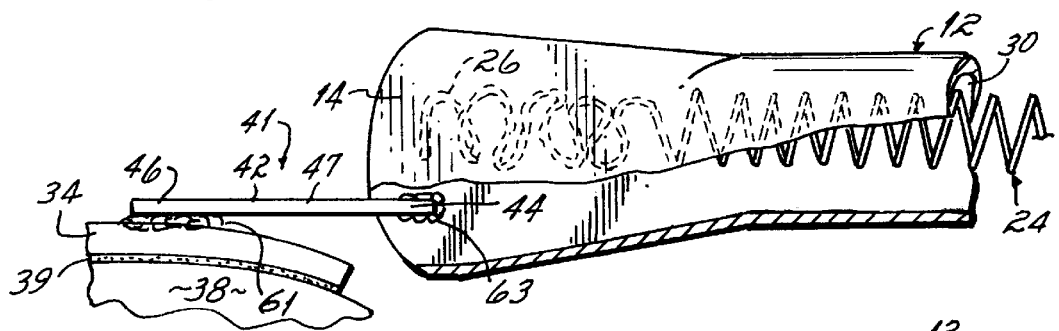
FIG. 2A is a view, similar to FIG. 2, showing an alternative embodiment of an attachment structure for attaching the orthodontic device to a tooth.

With reference to FIG. 2A, an embodiment of the flexible connection 41 that may be utilized to interconnect, for example, mounting pad 34 with tube 12 is illustrated. The flexible connection 41 comprises a short length of a bendable wire 42 having an unattached section 47 extending between a first end 44 and a second end 46. A side wall portion of the first end 44 is attached to an interior of the first tube 12 and a side wall portion of the second end 46 is attached to the mounting pad 34. The attachment of the first and second ends 44, 46 to the first tube 12 and mounting pad 34, respectively, may be accomplished by conventional securing methods such as adhesive bonding, welding, brazing, and soldering. Mounting pad 34 is affixed to tooth 38 using a quantity 39 of the dental adhesive. Because the action of second tube 18 sliding within first tube 12 produces a substantially linear motion, the flexible connection 41 allows device 10 to conform to the natural curvature of the archform of a patient's teeth and, thereby, prevents binding of the device 10. The flexible connection 41 can also accommodate a tooth rotation such that the device 10 can be attached to a rotated tooth and adjusted by bending as the tooth is rotated into a proper orientation by the corrective force applied by spring 24. The second end 46 of flexible connection 41 may be lengthened to extend beyond the attachment to pad 34 and shaped into a loop or a hook (not shown) so as to provide an attachment point for a secondary band or chain, as illustrated in FIGS. 1 and 2 with regard to the ends 26, 28 of spring 24. It is understood that the flexible connection 41 may be implemented in combination with various ones of the attachment methods for device 10 described above.

Figure 2B:
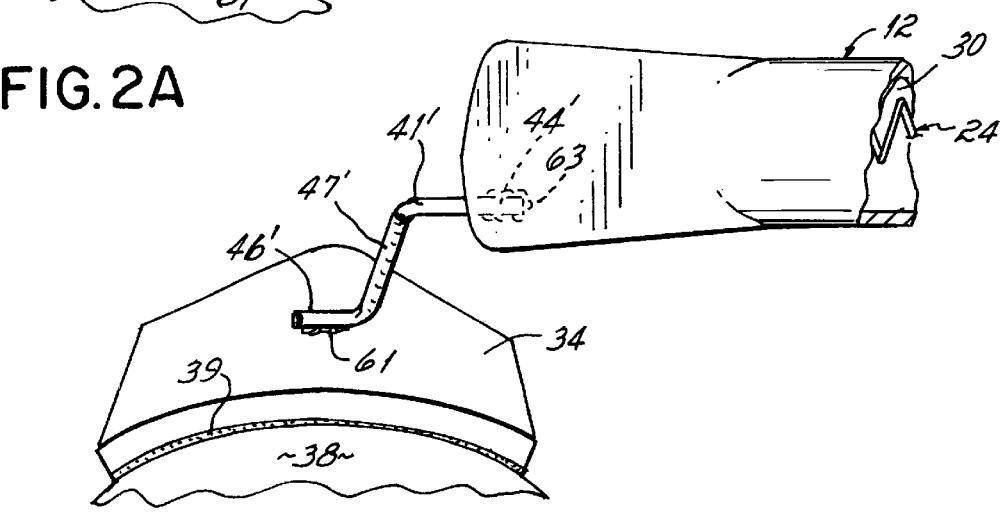
FIG. 2B is a view, similar to FIG. 2, showing another alterative embodiment an attachment structure for attaching the orthodontic device to a tooth.

With reference to FIG. 2B in which like reference numeral refer to like features in FIG. 2A, another embodiment of the flexible connection 41' has a lengthened unattached section 47' and is deformed, for example, to offset the device 10 from the tooth 38. The unattached section 47' of flexible connection 41' extends between a first end 44' and a second end 46'. A side wall portion of the first end 44' is attached to an interior of the first tube 12 and a side wall portion of the second end 46' is attached to the mounting pad 34. The attachment of the first and second ends 44', 46' to the first tube 12 and mounting pad 34, respectively, may be accomplished by conventional securing methods such as adhesive bonding, welding, brazing, and soldering. In this embodiment, the flexible connection 41' permits the orthodontic device 10 to be offset vertically from mounting pad 34 so as to maintain an adequate spacing between the device 10 and, for example, the gingival tissue if the mounting pad 34 is attached to tooth 38 near the gum line.

Referring to FIGS. 4–6, an intra-arch orthodontic device 60 constructed according to the present invention to expand the space between adjacent teeth in a single quadrant of a patient's mouth will be described. As shown in FIG. 4, device 60 is comprised of a pin 68 and a guide tube 62 having an open first end 64 and a second end 66, which may be substantially closed. The inner diameter of the tube 62 is slightly larger than the outer diameter of pin 68 so as to permit a sliding fit therebetween. The pin 68 has a first end 70 and a second end 72 that is slidably inserted into the first end 64 of tube 62 such a length of the second end 72 of the pin 68 projects from the opening in the first end 64. A compression spring 74 is disposed within tube 62 such that a first end 76 of the spring 74 is in contact with the second end 66 of the tube 62 and a second end 78 of the spring 74 contacts the first end 70 of the pin 68. The second end 78 of spring 74 is diametrically smaller than the first end 70 of pin 68 so that the pin 68 cannot slide into the open space circumscribed by the coils of the spring 74.

Mounting pads 80 and 82 are attached to the second ends 66 and 72 of the tube 62 and pin 68, respectively, so that device 60 may be attached to a patient's teeth 84, 86. Mounting pads 80, 82 have a foil and mesh construction typical of the type used in orthodontics and may be fabricated from an ASTM 316 austenitic steel. The mounting pads 80, 82 are attached to the tube 62 and pin 68, respectively, by respective quantities 81, 83 of a dental adhesive. It is understood by those of ordinary skill in the art of dentistry that by other conventional methods of attachment may be utilized to attach device 60 to teeth 84, 86. Such conventional attachment structures are described above with regard to device 10 and are contemplated by the present invention for attachment of device 60 to teeth 84, 86.

Tube 62 and pin 68 are made from a metal or metal alloy, such as a stainless steel, titanium or brass. An exemplary stainless steel is a AISI 304 stainless steel. Spring 74 may be constructed or fabricated from any metal or metal alloy suitable for constructing a compression spring, including stainless spring steel alloys, titanium alloys, and any alloy exhibiting pseudoelastic properties. Exemplary pseudoelastic alloys include, but are not limited to, nickel-titanium alloys. In one embodiment, spring 74 is constructed so that it is not permanently deformed or set after being expanded more than about 100 percent of its free length. In another embodiment, spring 74 is constructed to provide about 1500 grams, or less, of spring force to a patient's teeth when installed.

To facilitate installation of device 60 within a patient's mouth, the initial distance between mounting pads 80, 82 may be preset prior to installation and held in place with an activation structure 96 until the mounting pads have bonded securely to the teeth. In one embodiment and as illustrated in FIG. 4, the activation structure 96 is a ligature wire that is removably attached, such as by wrapping, between the peripheral second end 72 of the pin 68 and the peripheral second end 76 of the tube 62. The activation structure 96 holds the pin 68 in a stationary locked condition relative to tube 62 so as to prevent relative telescoping, sliding movement therebetween. When the activation structure 96 is removed by, for example, cutting with a cutting tool, the pin 68 assumes a released condition relative to the tube 62 for sliding relative movement so as to apply biasing forces to the patient's teeth 84, 86.

Referring to FIGS. 4 and 6, the operation of an intra-arch orthodontic device 60 will now be described. Device 60 is installed to a spaced-apart pair of teeth in a single quadrant of a person's mouth to correct malocclusions of the type in which it is desired to expand the spacing between adjacent ones of the teeth. Mounting pads 80 and 82 are fixed to a patient's teeth 84, 86 by bonding the pads to the teeth with respective quantities 39 of a dental adhesive. Mounting pad 82 is generally fixed to a molar tooth 86 to serve as an anchor, and mounting pad 80 is generally fixed to the tooth desired to be moved 84. The initial distance between mounting pads 80, 82 may be determined by using a model of the patient's teeth or any other suitable method such as reference to x-rays. Force is applied to device 60 to position the mounting pads 80, 82 at the desired distance and activation structure 96 is connected between tube 62 and pin 68, such that the pin 68 cannot telescopically move relative to the first tube 62 under the biasing force applied by the spring 74. With the mounting pads thus fixed in position, device 60 is installed onto the patient's teeth 84, 86 using respective quantities 81, 83 of dental adhesive, as described above.

Once the dental adhesive has cured, activation device 96 is removed, generally by cutting with a suitable implement or tool, whereby mounting pads 80 and 82 are biased in a direction away from one another under the biasing force of spring 74. In this manner, spring 74 applies a corrective force to the patient's teeth 84, 86 in a direction that moves the teeth apart and that expands the spaces between adjacent ones of teeth 84, 85a, 85b, 86, as depicted in FIG. 6. Because the relative motion of the mounting pads 80, 82, as constrained by the sliding contact of tube 62 and pin 68, is linear, device 60 may be installed to a patient's teeth 84, 86 so that the movement of a tooth 84 or 86 is purely translational, without any rotation or tipping of the tooth 84 or 86. Furthermore, since mounting pads 80, 82 are bonded directly to the teeth 84, 86, device 60 does not require an arch wire to be installed in the patient's mouth and therefore device 60 may be installed to either the labial or lingual side of a patient's teeth 84, 86.

While the present invention has been illustrated by a description of the preferred embodiments and while these embodiments have been described in some detail, it is not the intention of the Applicant to restrict or in any way limit the scope of the appended claims to such detail. Additional advantages and modifications will readily appear to those skilled in the art. Various features of the embodiments described herein may be combined in different manners depending on the desired characteristics. This has been a description of the present invention, along with the preferred methods of practicing the present invention as currently known. However, the invention itself should only be defined by the appended claims, wherein I claim:

What is claimed is:

1. An orthodontic device for adjusting the distance between a first tooth and a second tooth located in a single quadrant of a mouth, comprising:
   an outer tube having a first end, an open second end, a hollow interior, and a first longitudinal axis extending along the hollow interior between the first end and the second end, the first end adapted to be mounted to the first tooth;
   an inner tube having a third end, a fourth end, and a second longitudinal axis extending between the third end and the fourth end, the third end slidably received within the second end of the outer tube to form an enclosed space and the fourth end adapted to be mounted to the second tooth; and
   a spring positioned in the enclosed space, the spring biasing the inner tube toward the first end of the outer tube in a direction substantially parallel to the first and the second longitudinal axes, wherein said spring adjusts the distance between the first tooth and the second tooth located in the single quadrant when said orthodontic device is mounted thereto.

2. The orthodontic device of claim 1, wherein the spring is an extension spring and the inner tube has a hollow interior and the third end is open, a portion of the spring being positioned within the hollow interior of the inner tube, one end of the spring being attached to the first end of the outer tube and a second end of the spring being attached to the fourth end of the inner tube so the spring is expanded therebetween.

3. The orthodontic device of claim 2, wherein the device is actuatable between a locked condition in which the inner tube cannot slidingly move a significant distance relative to the outer tube and a released condition in which the biasing force is applied between the first tooth and the second tooth, and further comprising a removable activation structure which is adapted to hold the inner tube and the outer tube in the locked condition until the activation structure is disengaged to provide the released condition.

4. The orthodontic device of claim 3, wherein the activation structure can be relocated after disengagement to a different position along the length of the inner tube so as to provide a stop to halt the movement of the inner tube relative to the outer tube at a predetermined separation distance between the first tooth and the second tooth.

5. The orthodontic device of claim 1, wherein the spring is made from a material selected from the group consisting of stainless spring steel alloys, titanium alloys, and pseudoelastic metal alloys.

6. The orthodontic device of claim 1, wherein the spring is an extension spring and is formed of a material having elastic properties that are not permanently exceeded when the spring is extended more than about 100% of its original length.

7. The orthodontic device of claim 1, wherein the first end of the outer tube is attachable proximate the center of resistance of the first tooth and the fourth end of the inner tube is attachable proximate the center of resistance of the second tooth such that the spring applies a biasing force without causing significant rotation of either of the first and second teeth when mounted thereto.

8. The orthodontic device of claim 1, wherein a portion of the spring adjacent at least one of the first end and the fourth end extends outside of the enclosed space and is shaped to permit the attachment of a secondary force-applying element.

9. The orthodontic device of claim 1, wherein the inner tube includes a plurality of positioning marks for indicating the relative position of the inner tube relative to the outer tube.

10. The orthodontic device of claim 1, wherein the spring applies a biasing force effective for adjusting the distance between the first tooth and the second tooth when mounted thereto.

11. The orthodontic device of claim 10, wherein the biasing force applied by the spring is less than about 1500 grams.

12. An orthodontic device for reducing the distance between a first tooth and a second tooth located in a single quadrant of a mouth, comprising:
an outer tube having a first end, an open second end, a hollow interior, and a first longitudinal axis extending along the hollow interior between the first end and the second end, the first end adapted to be mounted to the first tooth;
an inner tube having an open third end, a fourth end, a hollow interior, and a second longitudinal axis extending between the third end and the fourth end, the third end-slidably received within the second end of the outer tube so that the hollow interiors of the outer tube and the second tube form an enclosed space, and the fourth end adapted to be mounted to the inner tooth;
a spring positioned in the enclosed space, one end of the spring being attached to the first end of the outer tube and a second end of the spring being attached to the fourth end of the inner tube so the spring is expanded therebetween, the spring biasing the inner tube toward the outer tube in a direction substantially parallel to the first and the second longitudinal axes, the device actuatable between a locked condition in which the inner tube cannot slidingly move a significant distance relative to the outer tube and a released condition in which a biasing force is applied between the first tooth and the second tooth when mounted thereto; and
an activation structure which is adapted to hold the inner tube and the outer tube in the locked condition until the activation structure is disengaged to provide the released condition.

13. The orthodontic device of claim 12, wherein the activation structure is an annular ring having an inner diameter sized to compressively engage an outer diameter of the inner tube, the compressive engagement sufficient to prevent movement of the inner tube relative to the outer tube under a biasing force applied by the spring.

14. The orthodontic device of claim 13, wherein the annular ring is fabricated from a material selected from the group consisting of a metal, a metal alloy, and an elastomer.

15. The orthodontic device of claim 12, wherein the activation structure compressively engages the outer diameter of the inner tube by a releaseable engagement such that the activation structure can be moved after disengagement to a different position along the length of the inner tube.

16. The orthodontic device of claim 12, wherein the spring is made from a material selected from the group consisting of stainless spring steel alloys, titanium alloys, and pseudoelastic metal alloys.

17. The orthodontic device of claim 12, wherein the spring is an extension spring.

18. The orthodontic device of claim 12, wherein the spring is formed of a material having elastic properties that are not permanently exceeded when the spring is extended more than about 100% of its original length.

19. An orthodontic device for increasing the distance between a first tooth and a second tooth located in a single quadrant of a mouth, comprising:
a guide tube having a first end, an open second end, a hollow interior, and a first longitudinal axis extending along the hollow interior between the first end and the second end, the first end adapted to be mounted to the first tooth;
a pin having a third end, a fourth end, and a second longitudinal axis extending between the third end and the fourth end, the pin having an outer diameter smaller than an inner diameter of the guide tube, the third end slidably received within second end of the guide tube to form an enclosed space, and the fourth end adapted to be mounted to the second tooth;
a spring positioned in the enclosed space, the spring biasing the pin relative to the guide tube in a direction substantially parallel to the first and the second longitudinal axes, the device actuatable between a locked condition in which the pin cannot slidingly move a significant distance relative to the guide tube and a released condition in which a biasing force is applied between the first tooth and the second tooth when mounted thereto; and
an activation structure which is adapted to hold the pin and the guide tube in the locked condition until the activation structure is removed to provide the released condition.

20. The orthodontic device of claim 19, wherein the activation structure is a ligature wire joining the third end of the pin and the second end of the guide tube, the ligature wire preventing the pin from moving relative to the guide tube until removed.

21. The orthodontic device of claim 19, wherein the spring is made from a material selected from the group consisting of stainless spring steel alloys, titanium alloys, and pseudoelastic metal alloys.

22. The orthodontic device of claim 19, wherein the spring is a compression spring.

23. An orthodontic device for adjusting the distance between a first tooth and a second tooth located in a single quadrant of a mouth, comprising:
an outer tube having a first end and an open second end, the first end adapted to be mounted to the first tooth;
an inner tube having a third end and a fourth end, the third end slidably received within the second end of the outer tube to form an enclosed space and the fourth end adapted to be mounted to the second tooth; and
a spring positioned in the enclosed space, the spring biasing the inner tube toward the first end of the outer tube, wherein said spring adjusts the distance between the first tooth and the second tooth located in the single quadrant when said orthodontic device is mounted thereto.

24. The orthodontic device of claim 23, further comprising a first mounting structure adapted to be mounted to the first tooth and a second mounting structure adapted to be mounted to the second tooth, the outer tube being attached to a portion of the first mounting structure and the inner tube being attached to a portion of the second mounting structure.

25. The orthodontic device of claim 24, further comprising a first flexible connection connecting the outer tube with the first mounting structure, wherein the first flexible connection allows the position of the orthodontic device to be adjusted relative to the first tooth when the outer tube is mounted thereto.

26. The orthodontic device of claim 25, wherein a central section of the first flexible connection is shaped to angularly offset the outer tube from the first mounting structure.

27. The orthodontic device of claim 25, wherein the first flexible connection comprises a cylindrical wire formed of a deformable metal.

28. The orthodontic device of claim 24, wherein the first mounting structure and the second mounting structure are structures selected from the group consisting of a welded joint, a brazed joints, a quantity of a dental adhesive, a soldered joint, an orthodontic band, a buccal tube, a dental bracket, and combinations thereof.

29. The orthodontic device of claim 14, further comprising a second flexible connection connecting the inner tube with the second mounting structure, wherein the second flexible connection allows the position of the orthodontic device to be adjusted relative to the second tooth when the inner tube is mounted thereto.

30. The orthodontic device of claim 29, wherein a central section of the second flexible connection is shaped to angularly offset the inner tube from the second mounting structure.

31. The orthodontic device of claim 29, wherein the second flexible connection comprises a cylindrical wire formed of a deformable metal.

32. The orthodontic device of claim 23 wherein the spring has a first portion and a second portion opposite the first portion, the first portion being attached to the outer tube and the second portion being attached to the inner tube, wherein the spring is expanded by the attachment between the outer tube and the inner tube.

33. The orthodontic device of claim 32 wherein the first portion of the spring is attached to the outer tube at the first end.

34. The orthodontic device of claim 33 wherein the second portion of the spring is attached to the inner tube at the fourth end.

35. The orthodontic device of claim 23 wherein the spring applies a spring bias capable of urging the inner tube toward the outer tube for decreasing the distance between the first tooth and the second tooth when mounted thereto.

36. An orthodontic device for reducing the distance between a first tooth and a second tooth located in a single quadrant of a mouth, comprising:
    an outer tube adapted to be mounted to the first tooth;
    an inner tube adapted to be mounted to the second tooth, the inner tube slidably received within the outer tube to form an enclosed space and movable relative to the outer tube in a telescoping relationship;
    a spring positioned in the enclosed space, the spring applying a biasing force capable of moving the inner tube relative to the outer tube, wherein said spring reduces the distance between the first tooth and the second tooth located in the single quadrant when said orthodontic device is mounted thereto; and
    an activation structure attached to the inner tube for preventing relative movement of the inner tube relative to the outer tube, the activation structure being removable from the inner tube for permitting the biasing force applied by the spring to move the inner tube relative to the outer tube.

37. The orthodontic device of claim 36, wherein the activation structure is an annular ring having an inner diameter sized to compressively engage an outer diameter of the inner tube, the compressive engagement sufficient to prevent movement of the inner tube relative to the outer tube under the biasing force applied by the spring.

38. The orthodontic device of claim 37, wherein the annular ring is fabricated from a material selected from the group consisting of a metal, a metal alloy, and an elastomer.

39. The orthodontic device of claim 36, wherein the activation structure is movable among multiple different positions along the inner tube.

40. An orthodontic device for increasing the distance between a first tooth and a second tooth located in a single quadrant of a mouth, comprising:
    a guide tube adapted to be mounted to the first tooth;
    a pin adapted to be mounted to the second tooth, the pin slidably received within the guide tube to form an enclosed space and movable relative to the guide tube in a telescoping relationship;
    a spring positioned in the enclosed space, the spring applying a biasing force capable of moving the pin relative to the guide tube, wherein said spring increases the distance between the first tooth and the second tooth located in the single quadrant when said orthodontic device is mounted thereto; and
    an activation structure preventing relative movement of the pin relative to the guide tube, the activation structure being removable for permitting the biasing force applied by the spring to move the pin relative to the guide tube.

41. The orthodontic device of claim 40, wherein the activation structure is a ligature wire joining the pin and the guide tube, the ligature wire preventing the pin from moving relative to the guide tube until removed.

* * * * *

UNITED STATES PATENT AND TRADEMARK OFFICE
CERTIFICATE OF CORRECTION

PATENT NO.    : 6,655,959 B2
DATED         : December 2, 2003
INVENTOR(S)   : Farrokh Farzin-Nia et al.

It is certified that error appears in the above-identified patent and that said Letters Patent is hereby corrected as shown below:

<u>Column 1,</u>
Line 49, change "an" to -- a --.

<u>Column 3,</u>
Line 46, insert -- of -- after "embodiment".

<u>Column 4,</u>
Line 24, change "adhesives" to -- adhesive --.
Line 52, change "38a, 40" to -- 38, 40a --.

<u>Column 5,</u>
Line 5, delete the first occurrence of "permit".
Line 21, delete "a".
Line 30, insert -- be -- after "may".

<u>Column 6,</u>
Line 59, insert -- of -- after "length".

<u>Column 8,</u>
Line 14, change "numeral" to -- numerals --.
Line 42, insert -- that -- after "such".
Line 60, change "by" to -- any --.

<u>Column 10,</u>
Line 2, change "Applicant" to -- Applicants --.
Line 11, change "I" to -- we --.

<u>Column 11,</u>
Line 35, change "second" to -- inner --.
Line 36, change "inner" to -- second --.

UNITED STATES PATENT AND TRADEMARK OFFICE
CERTIFICATE OF CORRECTION

PATENT NO. : 6,655,959 B2
DATED : December 2, 2003
INVENTOR(S) : Farrokh Farzin-Nia et al.

It is certified that error appears in the above-identified patent and that said Letters Patent is hereby corrected as shown below:

Column 13,
Line 18, change "joints" to -- joint --.
Line 21, change "14" to -- 25 --.

Signed and Sealed this

Twenty-sixth Day of July, 2005

JON W. DUDAS
*Director of the United States Patent and Trademark Office*